US00PP15615P2

(12) United States Plant Patent
Heuger

(10) Patent No.: US PP15,615 P2
(45) Date of Patent: Mar. 1, 2005

(54) ***HELLEBORUS* PLANT NAMED 'HGC JOSEF LEMPER'**

(50) Latin Name: *Helleborus niger*
Varietal Denomination: HGC Josef Lemper

(76) Inventor: Joseph Heuger, Münsterstrasse 49, 49129 Glandorf (DE)

( * ) Notice: Subject to any disclaimer, the term of this patent is extended or adjusted under 35 U.S.C. 154(b) by 0 days.

(21) Appl. No.: 10/878,417

(22) Filed: Jun. 28, 2004

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Datbase, GTI Jouve Retrieval Software 2004/40 Citation(s) for 'HGC Josef Lemper'.*

Huxley, Anthony, ed. RHS Dictionary of Gardening, vol. 2 D–K. New York: The Stockton Press: 1992. pp. 538–542.*

Wayside Gardens Autumn Catalog 1999; cover, last page and p. 72.*

Seyring, M. In vitro cloning of *Helleborus niger.* Plant Cell Reports 20 (10); p. 895–900 Mar. 2002 (abstract).*

Sunset National Garden Book Mar. 1997, Sunset Books, Menlo Park CA, p. 331.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Helleborus* plant named 'HGC Josef Lemper', characterized by its upright plant habit; dark green-colored leaves; large white-colored flowers; and relatively early flowering.

1 Drawing Sheet

Botanical classification/cultivar designation: *Helleborus niger* cultivar HGC Josef Lemper.

BACKGROUND OF THE INVENTION

The present Invention relates to a new and distinct cultivar of *Helleborus* plant, botanically known as *Helleborus niger*, and hereinafter referred to by the cultivar name HGC Josef Lemper.

The new *Helleborus* is a product of a planned breeding program conducted by the Inventor in Glandorf, Germany. The objective of the breeding program was to create new *Helleborus* cultivars with a good plant habit, that flower for a long period of time, and have attractive flower coloration.

The new *Helleborus* originated from a cross-pollination made by the Inventor in November, 1997 in Glandorf, Germany of an unnamed seedling of *Helleborus niger*, not patented, as the female, or seed, parent with an unnamed seedling of *Helleborus niger*, not patented, as the male, or pollen, parent. The new *Helleborus* was discovered and selected by the Inventor as a flowering plant within the progeny of the stated cross-pollination in a controlled environment in Glandorf, Germany.

Asexual reproduction of the new cultivar by divisions at Glandorf, Germany since March, 2000, has shown that the unique features of this new *Helleborus* are stable and reproduced true to type in successive generations.

SUMMARY OF THE INVENTION

Plants of the cultivar HGC Josef Lemper have not been observed under all possible environmental conditions. The phenotype may vary somewhat with variations in environment such as temperature and light level without, however, any variance in genotype.

The following traits have been repeatedly observed and are determined to be the unique characteristics of 'HGC Josef Lemper'. These characteristics in combination distinguish 'HGC Josef Lemper' as a new and distinct cultivar of *Helleborus:*

1. Upright plant habit.
2. Dark green-colored leaves.
3. Large white-colored flowers.
4. Relatively early flowering.

Plants of the new *Helleborus* flower about one month earlier than plants of the female parent. Compared to plants of the male parent, plants of the new *Helleborus* have larger flowers and flowered about one month later.

Plants of the new *Helleborus* can be compared to the *Helleborus niger* cultivar HGC Jericho, disclosed in U.S. Plant patent application Ser. No. 10/878,420. In side-by-side comparisons conducted in Glandorf, Germany, plants of the new *Helleborus* differed from plants of the cultivar HGC Jericho in the following characteristics:

1. Plants of the new *Helleborus* were taller than plants of the cultivar HGC Jericho.
2. Plants of the new *Helleborus* had longer leaf petioles than plants of the cultivar HGC Jericho.
3. Plants of the new *Helleborus* had larger flowers than plants of the cultivar HGC Jericho.
4. Flowers of plants of the new *Helleborus* had fewer sepals than flowers of plants of the cultivar HGC Jericho.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Helleborus*.

The photograph at the top of the sheet comprises a side perspective view of a typical flowering plant of 'HGC Josef Lemper'.

The photograph at the bottom of the sheet is a close-up view of a typical developing flower of 'HGC Josef Lemper'.

DETAILED BOTANICAL DESCRIPTION

The aforementioned photographs, following observations and measurements describe plants grown in Glandorf, Germany, in a glass-covered greenhouse and under commercial production practices during the winter. Plants were grown in 15-cm containers and were about six months old when the photographs and description were taken. During the production of the plants, day temperatures were about 18° C. and night temperatures were about 14° C. In the following description, color references are made to The Royal Horticultural Society Colour Chart, 1995 Edition, except where general terms of ordinary dictionary significance are used.

Botanical classification: *Helleborus niger* cultivar HGC Josef Lemper.

Parentage:

*Female parent*.—Unnamed seedling of *Helleborus niger*, not patented.

*Male parent*.—Unnamed seedling of *Helleborus niger*, not patented.

Propagation:

*Type*.—By divisions.

*Time to initiate roots, winter*.—About 40 days at 12° C.

*Time to produce a rooted plant, winter*.—About six months at 12 to 15° C.

*Root description*.—About 3 to 15 thick fleshy roots; not branching; white to brown in color.

Plant description:

*Plant form/habit*.—Upright plant habit; moderately vigorous growth habit. Leaves basal. Single flower form. Freely flowering habit.

*Plant height*.—About 27 cm.

*Plant width* (*spread*).—About 33 cm.

*Foliage description*.—Arrangement: Basal; palmately compound with six to nine leaflets per leaf. Leaflet length: About 4.5 to 8 cm. Leaflet width: About 2.5 to 3 cm. Leaflet shape: Lanceolate; pedate. Leaflet apex: Broadly acuminate. Leaflet base: Acute. Leaflet margin: Serrate. Texture, upper and lower surfaces: Smooth, glabrous. Venation pattern: Reticulate. Color: Developing leaflets, upper surface: 137A. Developing leaflets, lower surface: Closest to 147B. Fully expanded leaflets, upper surface: 137A. Fully expanded leaflets, lower surface: Closest to 147B. Venation, upper surface: 146C. Venation, lower surface: 146D. Petiole: Length: About 8 cm. Diameter: About 6 mm. Texture, upper and lower surfaces: Smooth, glabrous. Color, upper and lower surfaces: 145B slightly overlain with 175A.

Flower description:

*Flower type/habit*.—Single rounded flowers arranged singly on upright peduncles; flowers face upright to outwardly; petals inconspicuous. Freely flowering habit with about 15 flowers developing per plant at one time.

*Fragrance*.—Very slightly fragrant.

*Natural flowering season*.—Early flowering; intermittent flowering from October to February in Glandorf, Germany. Flowers persistent.

*Postproduction longevity*.—Flowers last about ten days on the plant.

*Flower buds*.—Height: About 2 cm. Diameter: About 1.2 cm. Shape: Ovoid. Color: 155A.

*Flowers*.—Diameter: About 9.5 cm. Depth: About 1.5 cm.

*Petals*.—Size: Minute, obscured by reproductive organs; forming inconspicuous nectaries.

*Sepals*.—Quantity/arrangement per flower: Typically five in a single whorl. Length: About 4.5 cm. Width: About 4 cm. Shape: Broadly ovate. Apex: Rounded. Margin: Entire. Texture, upper and lower surfaces: Smooth, glabrous; satiny. Color: Developing sepals, upper and lower surfaces: More white than 155D; towards the base, 144B. Fully expanded sepals, upper and lower surfaces: More white than 155D; towards the base, 144B. Color becoming closer to 144A with development.

*Peduncles*.—Length: About 15 to 25 cm. Diameter: About 4 to 7 mm. Orientation: Upright. Strength: Strong. Texture: Smooth, glabrous. Color: 145B with spots, 183A.

*Pedicels*.—Not observed.

*Reproductive organs*.—Stamens: Quantity per flower: About 100. Anther shape: Oblong. Anther length: About 2 mm. Anther color: 153D. Pollen amount: None observed. Pistils: Quantity per flower: About nine. Pistil length: About 1.5 cm. Stigma shape: Tuberculate. Stigma color: 145C. Style length: About 9 mm. Style color: 145C. Ovary color: 145B to 145C.

*Seed/fruit*.—Seed and fruit development have not been observed.

Disease/pest resistance: Plants of the new *Helleborus* have not been noted to be resistant to pathogens and pests common to *Helleborus*.

Temperature tolerance: Plants of the new *Helleborus* have been observed to tolerate temperatures from −15 to 36° C.

It is claimed:

1. A new and distinct cultivar of *Helleborus* plant named 'HGC Josef Lemper', as illustrated and described.

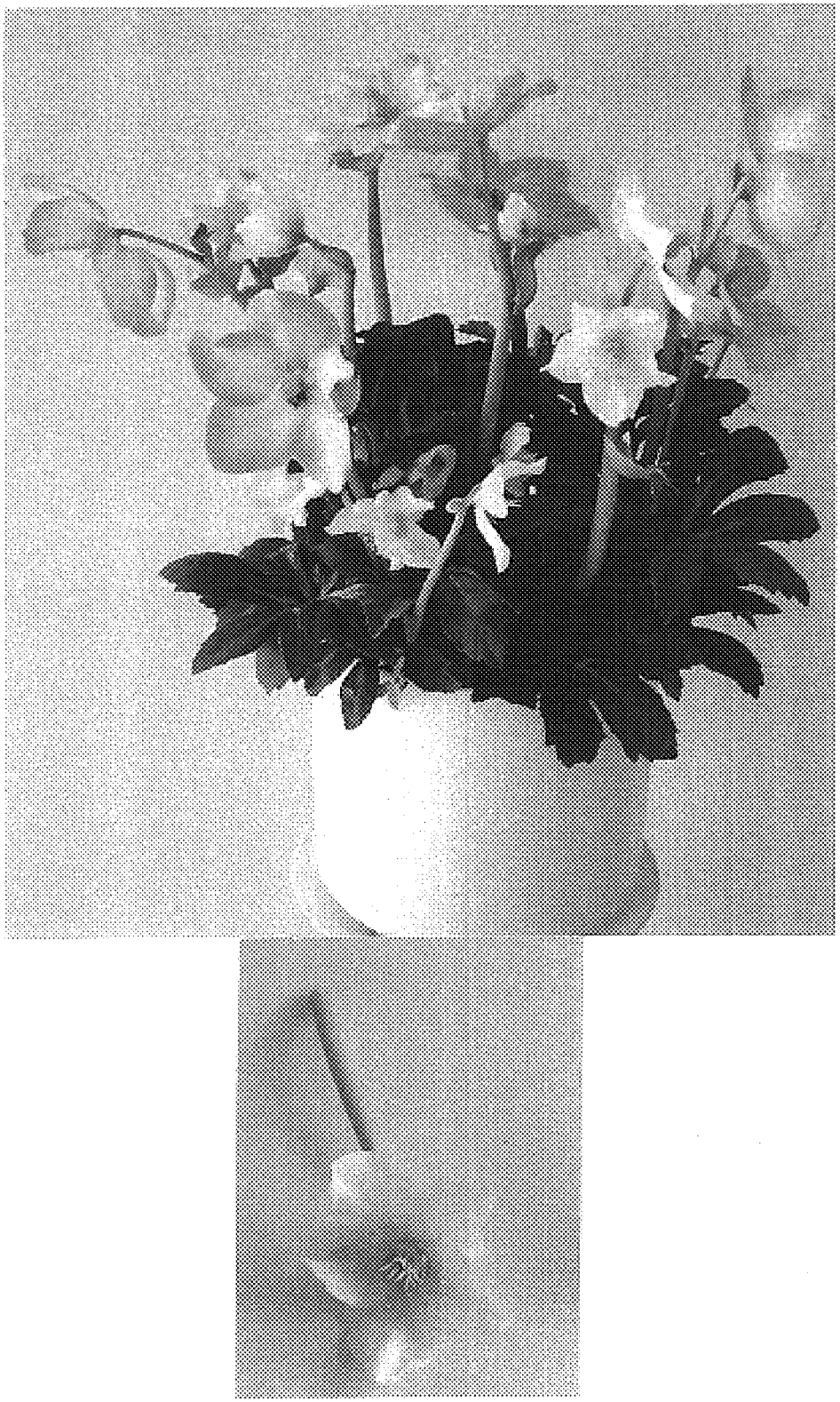

* * * * *